(12) United States Patent
Kharrat et al.

(10) Patent No.: US 7,150,183 B2
(45) Date of Patent: *Dec. 19, 2006

(54) COMPOSITIONAL CHARACTERIZATION AND QUANTIFICATION OF SOLID DEPOSITS FROM HYDROCARBON FLUIDS

(75) Inventors: Abdel M. Kharrat, Edmonton (CA); Mohammed I. Zougari, Edmonton (CA); Ahmed Hammami, Edmonton (CA); John Ratulowski, Missouri City, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 52 days.

This patent is subject to a terminal disclaimer.

(21) Appl. No.: 11/013,493

(22) Filed: Dec. 16, 2004

(65) Prior Publication Data

US 2005/0170516 A1    Aug. 4, 2005

Related U.S. Application Data

(63) Continuation-in-part of application No. 10/465,493, filed on Jun. 19, 2003, now Pat. No. 6,959,588.

(51) Int. Cl.
*G01N 33/00* (2006.01)
(52) U.S. Cl. .................................... 73/61.62
(58) Field of Classification Search ............... 73/61.62
See application file for complete search history.

(56) References Cited

U.S. PATENT DOCUMENTS

| 4,339,945 A * | 7/1982 | Knudsen et al. ........... 73/61.62 |
|---|---|---|
| 4,383,438 A | 5/1983 | Eaton |
| 4,878,382 A | 11/1989 | Jones et al. |
| 4,910,999 A | 3/1990 | Eaton |
| 5,161,409 A | 11/1992 | Hughes et al. |
| 5,309,761 A | 5/1994 | Ravi et al. |
| 5,339,845 A * | 8/1994 | Huddas ................. 134/169 A |
| 5,360,738 A | 11/1994 | Jones et al. |
| 5,361,631 A | 11/1994 | Covington et al. |
| 5,753,802 A | 5/1998 | Falkler |
| 5,959,194 A | 9/1999 | Nenniger |
| 6,062,069 A | 5/2000 | Panchal et al. |
| 6,311,546 B1 * | 11/2001 | Dickinson et al. ............. 73/37 |
| 6,535,796 B1 | 12/2003 | Sierro et al. |
| 6,959,588 B1 * | 11/2005 | Zougari et al. ............ 73/61.62 |
| 2004/0255649 A1 | 12/2004 | Zougari et al. |

FOREIGN PATENT DOCUMENTS

WO    WO 2004/111601 A2    12/2004

OTHER PUBLICATIONS

English language abstract for JP-61135913-A, published Jun. 1986.*

* cited by examiner

*Primary Examiner*—Michael Cygan
(74) *Attorney, Agent, or Firm*—Trop, Pruner & Hu, P.C.; Bryan P. Galloway; Jaime A. Castano

(57) ABSTRACT

A technique includes providing a deposition measuring device having a deposition from a fluid sample on an interior surface of the device. The technique also includes operating the device with a solvent to produce a solvent solution that contains the deposition. The solvent solution is used to quantify at least one chemical compound that is present in the deposition.

27 Claims, 5 Drawing Sheets

FIG. 7

| COMPOUND TYPE | ORIGINAL DEAD OIL | OSDC | | |
|---|---|---|---|---|
| | | PRODUCTION OIL | SPINDLE | WALL |
| N | 53.41979 | 52.53053 | 38.42 | 9.612102 |
| NS | 15.2267 | 18.77754 | 12.07 | 3.544142 |
| NO | 2.837789 | 2.643837 | 6.14 | 2.272435 |
| $N_2$ | 7.416797 | 11.09153 | 4.24 | 0.750107 |
| O | 5.392513 | 5.186957 | 1.99 | 1.336715 |
| NOS | 1.700282 | | 2.88 | 0.828696 |
| $N_2O$ | 3.153249 | 3.588065 | 2.85 | 0.751171 |
| $NO_2$ | 0.398 | | 3.29 | 2.856258 |
| $N_2S$ | 1.979141 | 3.065592 | 1.13 | |
| OS | 0.9727 | | 0.81 | 0.733348 |
| $NS_2$ | | 3.115951 | 1.92 | 0.205195 |
| $O_4S$ | 0.432 | | 10.08 | 33.2077 |
| $O_2$ | 1.04865 | | 3.46 | 4.80986 |
| $O_3S$ | 0.067 | | 2.27 | 8.6247 |
| $O_5S$ | 0.034 | | 1.79 | 7.886438 |
| $NO_2S$ | | | 0.94 | 0.436286 |
| $NO_3$ | 0.044 | | 0.50 | 1.240362 |
| $N_2O_2$ | | | 0.48 | |
| $O_2S$ | 0.012 | | 0.38 | 1.273264 |
| $O_3$ | | | 0.20 | 1.707381 |
| $O_6S$ | 0.063 | | 0.08 | 1.620789 |
| $O_7S$ | | | | 0.652052 |
| $O_8S$ | | | | 0.100134 |
| $O_3S_2$ | | | | 5.262528 |
| $O_4S_2$ | | | | 2.426194 |
| $O_5S_2$ | | | | 1.807834 |
| $O_6S_2$ | | | | 0.265279 |
| $NO_3S$ | | | | 0.109787 |
| $NO_4S$ | | | | 1.100024 |
| $NO_5S$ | | | | 0.191295 |
| $O_4$ | | | | 1.201329 |
| $NO_4$ | | | | 0.401171 |

COMPOSITIONAL CHARACTERIZATION AND QUANTIFICATION OF SOLID DEPOSITS FROM HYDROCARBON FLUIDS

This application is a continuation-in-part of U.S. patent application Ser. No. 10/465,493, entitled, "Couette Device And Method To Study Solids Deposition From Flowing Fluids," filed on Jun. 19, 2003.

BACKGROUND

The invention relates generally to compositional characterization and quantification of solid deposits from hydrocarbon fluids.

When fluids are transported by flowing through pipes or tubing, the deposition of solids from the fluid onto the interior walls of the pipes or tubing may impair fluid flow. An example of such a fluid is crude oil. Crude oil from many formations commonly contains solids, often as one or more of waxes, asphaltenes, sulfur, scale, and hydrates.

Paraffin waxes are essentially mixtures of long-chain n-paraffins with carbon chain lengths ranging from $C_{15}$ to $C_{75+}$.

Asphaltenes and residual oil components often co-precipitate with the paraffin waxes and result in varying appearance (color) and texture to the precipitated solids. Asphaltenes are generally compounds including more than about 70 carbon atoms, mostly in aromatic polycyclic clusters variably substituted with alkyl groups; asphaltenes may also contain heteroatoms (such as N, S, or O), metals (such as Ni, V, or Fe), or both. Hydrates generally include water molecules in an ice-like structure encaging one or more organic compounds. The organic compounds encaged by the ice-like structure are commonly methane, ethane, propane, or other alkenes with less than about 10 carbon atoms.

Under many conditions, the solids present in a fluid remain dissolved in the fluid. However, when a fluid, such as crude oil, is transported via pipe, such as from a geologic formation to a wellhead via production tubing or from a wellhead or a storage vessel to a refinery via a pipeline, changes in the pressure, temperature, composition, or other parameters of the flowing fluid may lead to precipitation and deposition of solids. Deposition in a pipe is generally undesirable, because deposited solids may at least partially block the pipe and lead to reductions in the flow rate of the fluid in the pipe and require expensive and time-consuming cleaning of the pipe to restore the maximum flow rate of the fluid.

Similar observations exist for other fluids which may contain solids. Such fluids, either liquids or gases, include fluids used in the industrial production of paint, food products, pharmaceuticals, plastics, and paper and paper products, among other industries.

The study of deposition is difficult for, among other reasons, the difference between fully turbulent flow (that is, flow that is both non-laminar and without the presence of vortices) of a sample fluid in a pipe and the sample fluid in a laboratory scale apparatus. Common laboratory scale apparatus are generally unable to provide conditions for fully turbulent flow as a result of limitations in apparatus geometry and design. Further, common laboratory scale apparatus generally cannot provide sufficient levels of pressure and shear to readily study the deposition of solids.

Thus, there exists a continuing need for better ways to simulate turbulent flow found in production tubing or pipeline under field conditions and recover solids that are deposited in this simulation for purposes of characterizing and quantifying the deposition.

SUMMARY

In an embodiment of the invention, a technique includes providing a deposition measuring device having a deposition from a fluid sample on an interior surface of the device. The technique includes operating the device with a solvent to produce a solvent solution that contains the deposition. The solvent solution is used to quantify at least one chemical compound that is present in the deposition.

Advantages and other features of the invention may become apparent from the following description, drawing and claims.

BRIEF DESCRIPTION OF THE DRAWING

FIG. 7 is a table depicting results of a exemplary quantification according to an embodiment of the invention.

DETAILED DESCRIPTION

Figure 1:
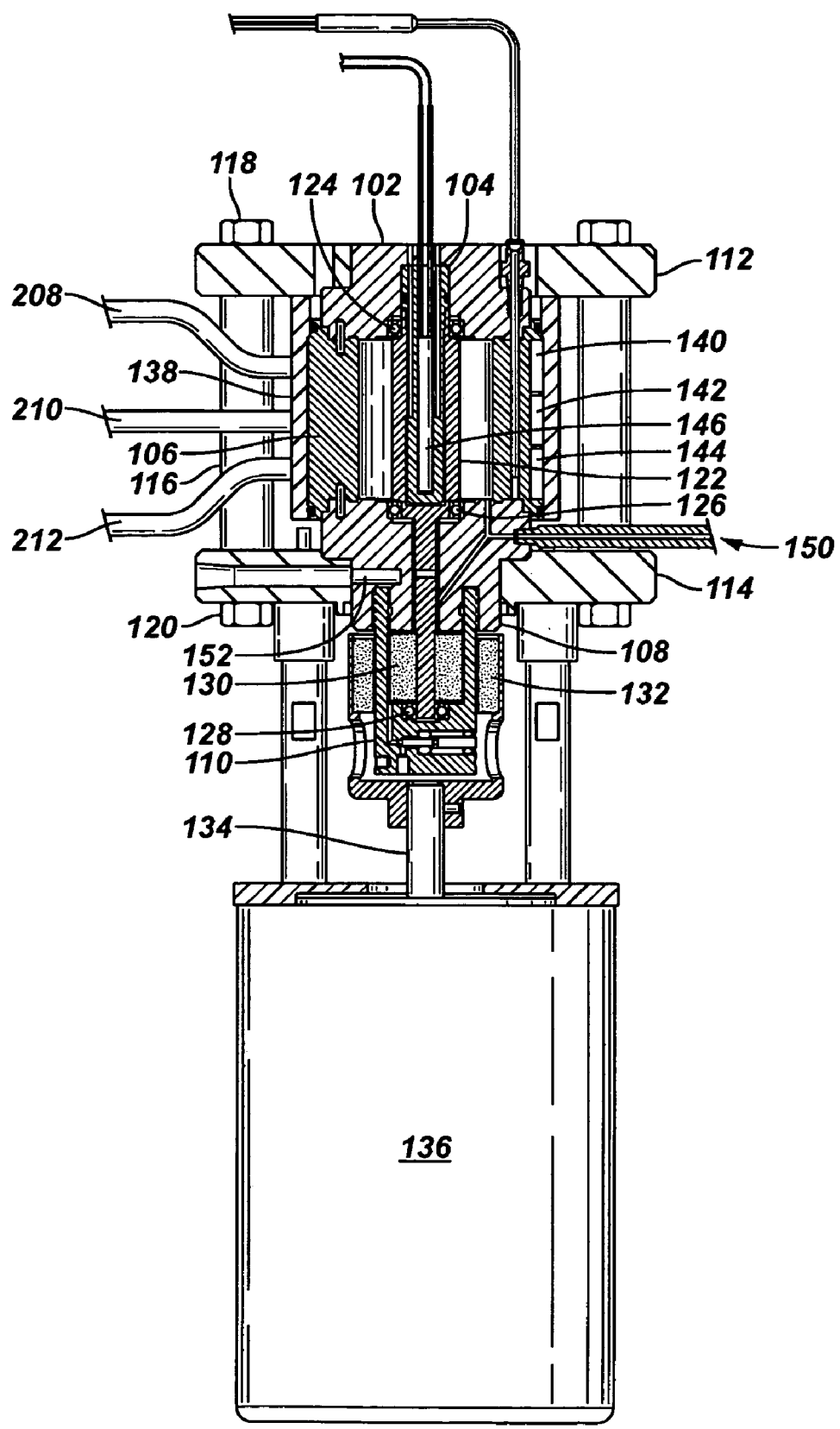
FIG. 1 is a cross-sectional view of a cylindrical Couette device according to an embodiment of the invention.

Described below are techniques to characterize the composition of solid deposits from hydrocarbon fluids as well as quantify these solid deposits. In some embodiments of the invention, the solids are deposited in a device called a Couette device. However, the solids may be collected by mechanisms other than a Couette device in other embodiments of the invention. Thus, the Couette device is first described below (as one out of many possible devices to collect a solid deposit); and thereafter, the techniques to characterize and quantify the solid deposit are described below.

In accordance with some embodiments of the invention, a Couette device is used to collect a deposition from a fluid sample under a simulated turbulent flow condition formed in a production tubing or a pipeline. The Couette device may have a number of different designs, an exemplary one of which is set forth below.

A Couette device is a device in which two or more walls define an annulus and in which an apparatus may impart Couette flow to a fluid (a gas or a liquid) occupying all or part of the annulus. A "cylindrical Couette device," as the term is used herein, refers to a device including an outer, hollow cylinder and an inner cylinder, which define an annulus in the volume between the exterior surface of the inner cylinder and the interior surface of the outer cylinder. These surfaces may be referred to herein as "annular walls." The term "cylinder" refers to an object having a substantially circular cross-section in a plane perpendicular to the axis of the object. By rotating the outer cylinder, the inner cylinder, or both relative to one another, Couette flow may be imparted to a fluid (a gas or a liquid) occupying all or part of the annulus. The Couette device further includes a sample inlet and a sample outlet for charging and draining the fluid from the annulus. The sample inlet and the sample outlet may be separate ports or the same port. The sample inlet may include a pressure regulator capable of charging the annulus to a defined pressure of the fluid. Examples of Couette devices include the cylindrical Couette device disclosed by Nenninger, U.S. Pat. No. 5,959,194.

The amount of shear generated by a Couette device may be characterized by a Reynolds number. The Reynolds number for a cylindrical Couette device, wherein the inner cylinder rotates and outer cylinder is stationary relative thereto, with a particular fluid therein may be represented as $R_e=(\omega \rho/\mu) r_i (r_o - r_i)$, wherein $\omega$ is the rotational speed, $\rho$ is the density of the fluid, $\mu$ is the dynamic viscosity of the fluid, $r_i$ is the radius of the inner cylinder, and $r_o$ is the radius of the outer cylinder. "Fully turbulent flow," as the term is used herein, refers to flow that is both non-laminar and free of vortices.

In some embodiments of the invention, the Couette device includes an outer cylinder that is defined by a cylindrical wall that has an interior surface and an exterior surface. Affixed thereto are a top wall having an interior surface and an exterior surface and a bottom wall that has an interior surface and an exterior surface. Generally, the outer cylinder, the top wall, and the bottom wall may define a pressure containment zone. Typically, in the top wall, the bottom wall, or both, there may be a mounting apparatus for mounting the inner cylinder, and a seal for sealing the joint of the inner cylinder and the top or bottom wall.

In some embodiments of the invention, the shortest distance between the axis of the outer cylinder and the interior surface of the cylindrical wall may be defined as a radius $r_o$.

The outer cylinder may be fabricated from any suitable material. In some embodiments of the invention, the outer cylinder may be fabricated from a sour-fluid-resistant alloy. A "sour-fluid-resistant alloy" means a material including one or more metals and is resistant to corrosive materials that may be present in crude oils or other fluids. Such corrosive materials include $H_2S$, among others. In a further embodiment, the outer cylinder may be fabricated from a nickel-chromium-iron alloy, such as is commercially available as Inconel®, Inco Ltd., Toronto, Ontario. In another embodiment of the invention, the outer cylinder may be fabricated from a stainless steel.

The outer cylinder may be machined to any appropriate specification of cylindrical perfection, interior surface roughness or smoothness, or size, among other parameters that may be apparent to the skilled artisan. In some embodiments of the invention, the cylindrical perfection and interior surface roughness or smoothness are sufficient to ensure turbulence in a sample of a fluid loaded to the annulus of the cylindrical Couette device.

The cylindrical Couette device includes an inner cylinder, as described above. The inner cylinder is defined by a cylindrical wall that has an exterior surface. Affixed thereto may be a top wall that has an exterior surface, a bottom wall that has an exterior surface, or both. The inner cylinder may also include a portion connected to or integral with the top wall, the bottom wall, or both which is capable of coupling to a matching coupling apparatus in the top wall, the bottom wall, or both of the outer cylinder.

In some embodiments of the invention, the inner cylinder may be rotatably connected to and coaxial with the outer cylinder. "Rotatably connected," as used herein, means that the inner cylinder is mounted to the outer cylinder in such a way that the inner cylinder, the outer cylinder, or both are free to rotate relative to one another. "Coaxial" has the meaning that the axis of the inner cylinder and the axis of the outer cylinder both lie along substantially the same line.

In some embodiments of the invention, the inner cylinder is coupled to the top wall of the outer cylinder by one or more bearings.

In some embodiments of the invention, the inner cylinder may contain a heat source. The heat source may be integral with the inner cylinder or wholly or partially surrounded by other components of the inner cylinder. Exemplary heat sources include a heating cartridge and viscous heating (i.e., frictional heating generated at the boundary between the rotating cylinder and a fluid present in the annulus), among others.

In some embodiments of the invention, the heat source is a heater cylinder, defined by a cylindrical wall having an exterior surface. The heater cylinder may be connected to the outer cylinder and located in the interior of the inner cylinder. The heater cylinder may have a radius $r_h$, defined as the shortest distance between the axis of the heater cylinder and the exterior surface of the heater cylinder cylindrical wall, and $r_h < r_i$. The heater cylinder may itself define a chamber in which a heater cartridge may be located. The heater cylinder may be closed at either or both ends or open at either or both ends as a matter of routine experimentation to the skilled artisan having the benefit of the present disclosure. In some embodiments of the invention, the heater cylinder is open at one end, to allow insertion of a heater cartridge into the heater cylinder while allowing the other, closed end to form a part of the pressure containment of the Couette device. If the heater cylinder is housed within the inner cylinder, the heater cylinder may be fixed relative to the inner cylinder, fixed relative to the outer cylinder, or unfixed relative to either cylinder.

The inner cylinder may be fabricated from any suitable material. In one embodiment, the inner cylinder may be fabricated from a sour-fluid-resistant alloy, such as a nickel-chromium-iron alloy, as described above. In another embodiment, the inner cylinder may be fabricated from a stainless steel. The inner cylinder may be machined to any appropriate specification of cylindrical perfection, exterior surface roughness or smoothness, or size, among other parameters that may be apparent to the skilled artisan. In one embodiment, the cylindrical perfection and exterior surface roughness or smoothness are sufficient to ensure turbulence in a sample of a fluid loaded to the annulus of the cylindrical Couette device.

The inner cylinder may have a radius $r_i$, defined as the shortest distance between the axis of the inner cylinder and the exterior surface of the inner cylinder wall. As may be apparent to the skilled artisan from the foregoing discussion of the cylindrical Couette device geometry, the $r_i$ radius (the radius of the inner cylinder) is less than $r_o$ (the radius of the outer cylinder). The ratio of $r_o/r_i$ may theoretically be any value greater than 1 and less than infinity. Typically, the value of $r_o/r_i$ may be in the range of from about 1.1 to about 3.0. In particular embodiments, the value of $r_o/r_i$ may be about 1.5, about 2.0, or about 2.5.

A spherical Couette device may generally be similar, with the primary differences being that the outer cylinder may instead be an outer sphere and the inner cylinder may instead be an inner sphere. A parallel Couette device may also generally be similar, with the primary differences being that the outer cylinder may instead be a first plate and the inner cylinder may instead be a second plate parallel to the first. Top and bottom end caps, as may be used in the cylindrical Couette device, may be dispensed with, replaced with functionally equivalent components, or changed in geometry in the spherical Couette device or the parallel Couette device. The outer cylinder of the cylindrical Couette device, the outer sphere of the spherical Couette device, and the first plate of the parallel Couette device may be considered homologous structures. The inner cylinder of the cylindrical Couette device, the inner sphere of the spherical Couette device, and the second plate of the parallel Couette device may be considered homologous structures.

As stated above, the outer cylinder and the inner cylinder of the cylindrical Couette device, or the homologous structures of other Couette devices, define an annulus. The annulus may also be referred to as a "pressure containment zone." An inlet and an outlet are provided, typically in the outer cylinder, such as in the top wall, bottom wall, or cylinder wall of the outer cylinder, although an inlet and an outlet in the inner cylinder are possible, to allow a fluid to be charged to the annulus and drained from the annulus. As stated above, the inlet and the outlet may be the same port or they may be different ports.

As stated above, the cylindrical Couette device includes a rotatable connector between the inner cylinder and the outer cylinder. The rotatable connector may be a magnetic coupling to connect the inner cylinder with a prime mover, such as a motor, without physical contact. The motor may rotate a magnet array. The magnet array may provide a magnetic coupling involving a magnetic field, through the outer cylinder wall, top wall, or bottom wall, between an outer and inner set of magnets. Upon rotation of the magnet array, a torque is imparted to one cylinder relative to the other resulting in its rotation. A magnetic coupling allows the inner cylinder and the outer cylinder to rotate relative to one another without the need of a dynamic seal, allowing higher pressures of fluid in the annulus and higher rotational speeds than a dynamic seal would allow. A magnetic coupling allows the inner cylinder and the outer cylinder to rotate relative to one another with less friction than is typically found when a physical seal, such as a gasket, O-ring, or the like, is used, thus allowing more efficient operation of the cylindrical Couette device.

The rotatable connector may, in some embodiments of the invention, include one or more bearings between the inner cylinder and the outer cylinder.

As stated above, the cylindrical Couette device also includes a motor or motors capable of rotating the inner cylinder, the outer cylinder, or both relative to one another. The motor or motors may be any appropriate motor known in the art, such as an electric motor.

Among other features, the Couette device may include a heat exchange jacket that envelops at least a portion of the outer cylinder and has an interior surface and an exterior surface. The exterior surface of the outer cylinder and the interior surface of the heat exchange jacket define a heat exchange fluid annulus in the space therebetween. The heat exchange jacket includes a heat exchange fluid inlet and a heat exchange fluid outlet, which may be the same port or different ports. A heat exchange fluid, which may be any fluid but is typically water, may serve to heat, cool, or maintain the temperature of the fluid inside the Couette device, and may be charged to the heat exchange fluid annulus via the heat exchange fluid inlet at a temperature at which it is desired to hold the Couette device or at a temperature and a flow rate which may keep the temperature of the Couette device at the desired temperature. Heat exchange fluid may then be drained from the heat exchange fluid annulus via the heat exchange fluid outlet. The heat exchange fluid may be at ambient pressure, reduced pressure, or elevated pressure, as appropriate depending on the heat exchange fluid and the desired temperature at which the Couette device is to be held.

In some embodiments of the invention, the Couette device includes one or more temperature sensors, such as one or more thermocouples or RTDs. The temperature sensor may be mounted in the inner cylinder, the outer cylinder, the top wall, the bottom wall, or two or more of the foregoing, in such a way as to report the temperature at one or more points in the inner cylinder, annulus, or outer cylinder.

In some embodiments of the invention, the Couette device may further include a torque sensor, such as a viscometer; or a shear sensor. The torque sensor may be mounted at any point where it may measure the torque generated in the Couette device; a convenient mounting point is on the shaft of the driving device. The shear sensor may be mounted on the inner cylinder, the outer cylinder, or both in such a way as to calculate the shear undergone by the fluid at one or more points in the annulus.

The Couette device may include other sensors, such as a heat exchange fluid inlet temperature sensor, a heat exchange fluid outlet temperature sensor, a heat exchange jacket pressure sensor, heat exchange fluid inlet and outlet pressure differential sensors, a heat exchange fluid flow rate sensor, an inner cylinder rotational speed sensor, a motor rotational speed sensor, or two or more of the foregoing, among others.

In some embodiments of the invention, the Couette device includes a displacement fluid inlet and a displacement fluid outlet. The displacement fluid inlet allows a displacement fluid to be charged to the annulus to expel a fluid sample from the annulus via the sample outlet. The displacement fluid inlet may include a pressure regulator capable of charging the displacement fluid to the annulus at a defined pressure. In some embodiments of the invention, the pressure regulator may charge the displacement fluid to the annulus at a pressure substantially equal to that of the fluid sample. The displacement fluid inlet may include a heater, a cooling device, or both to set the temperature of the displacement fluid. In some embodiments of the invention, the heater, the cooling device, or both may set the temperature of the displacement fluid to a temperature substantially equal to that of the fluid sample.

In some embodiments of the invention, the displacement fluid is helium. In other embodiments, other inert gases, mixtures thereof, or a mixture of solution gases from the sample fluid (a "solution gas mixture"), may be used.

Generally, the displacement fluid outlet may be the same port as the sample outlet, although a separate displacement fluid outlet may be provided, such as for venting an overpressure of displacement fluid from the annulus after the fluid sample has been expelled.

In some embodiments of the invention, the Couette device further includes a solvent inlet and a solvent outlet. The solvent inlet allows a solvent to be charged to the annulus and dissolve organic materials which may be present on the annular walls as a result of precipitation and deposition from a fluid sample, as further described below.

In some embodiments of the invention, the Couette device is capable of continuous operation, that is, sample fluid is continuously charged to the annulus and is simultaneously continuously withdrawn from the annulus. The rates of fluid charge and withdrawal may be the same or they may be different; if different, the pressure of the sample may increase if the rate of fluid charge is greater than the rate of fluid withdrawal and may decrease if the rate of fluid charge is less than the rate of fluid withdrawal.

The various inlets and outlets described above may include plugs, valves, pressure regulators, or other devices capable of regulating the charging or draining of sample fluid, displacement fluid, solvent, or heat exchange fluid. A single physical port may function as one, two, three, or more of the various inlets, outlets, or both described above.

The Couette device may also include a solution analysis device downstream of the solvent outlet. The solution analysis device may be a chromatograph or any other device capable of identifying, quantifying, or both particular organic compounds dissolved in the solution drained from the annulus via the solvent outlet. Exemplary solution analysis devices include, but are not limited to, gas chromatographs, high performance liquid chromatographs (HPLCs), gel permeation chromatography, nuclear magnetic resonance imagers (NMR), infrared spectroscopes, ultraviolet spectrophotometers, thin layer chromatographs, and column chromatographs, among others.

The Couette device may also include one or more analysis devices which detect the presence of solids in the fluid sample. These solids may include waxes, asphaltenes, and hydrates, as well as emulsions, such as water-in-oil emulsions. The analysis devices may include viscometers, quartz crystal microbalances, ultrasonic probes, light transmittance/scattering probes, temperature sensors, and electrical conductivity sensors, among others.

The Couette device may also include a composition altering device upstream of the sample inlet. A "composition altering device" is a device which may change the composition of the sample fluid. In one embodiment, the composition altering device is a continuous-flow mixer, such as a static mixer. As used herein, the term "change" refers to a controllable increase or decrease in the value of a process variable.

The Couette device may also include a controller, such as a computer capable of receiving inputs from the user, from a data-gathering device or devices within or around the Couette device, or both; performing calculations based on the inputs; and sending outputs to the user, to control an actuating device or devices around the Couette device, or any combination thereof. The inputs so received may include temperature, pressure, torque, cylinder rotational speed, sample composition, and deposit thickness and composition as a function of time, among others. The inputs may be received either in real time, offline, or both. The outputs so sent may be used to vary parameters of a test run via the actuating devices and report results. The parameters that may be varied may include temperature, pressure, torque, cylinder rotational speed, and sample composition, among others, and the reported results may include temperature, pressure, torque, cylinder rotational speed, sample composition, and deposit thickness and composition as a function of time, among others. The outputs may be sent either in real time, offline, or both. In addition to the controller, the Couette device may also include apparatus for transferring signals between the controller and any of the user, the data-gathering device or devices, and the actuating device or devices, among others. Signal transmission devices may include cables, wireless transmitters, and wireless receivers, among others.

In some embodiments of the invention, the reported results include temperature, pressure, torque, cylinder rotational speed, sample composition, surface type, surface roughness, and deposit composition.

Couette devices, according to some embodiments of the invention, provide pressure and shear comparable to field conditions, to readily study the deposition tendency and extent of solids.

"Comparable to field conditions" means that the pressure, shear, composition, and other parameters generated in the Couette devices of the present invention are each substantially equal or equivalent to the pressure, shear, composition, and other parameters which a fluid may undergo in industrial-scale transport or processing. The composition of a fluid may vary as a result of injecting new materials, mixing two or more materials, changing the phase of the fluid by increasing or decreasing the temperature or pressure of the fluid, or other techniques, thus simulating industrial scale events such as gas-lift or commingling, among others.

Figure 2:
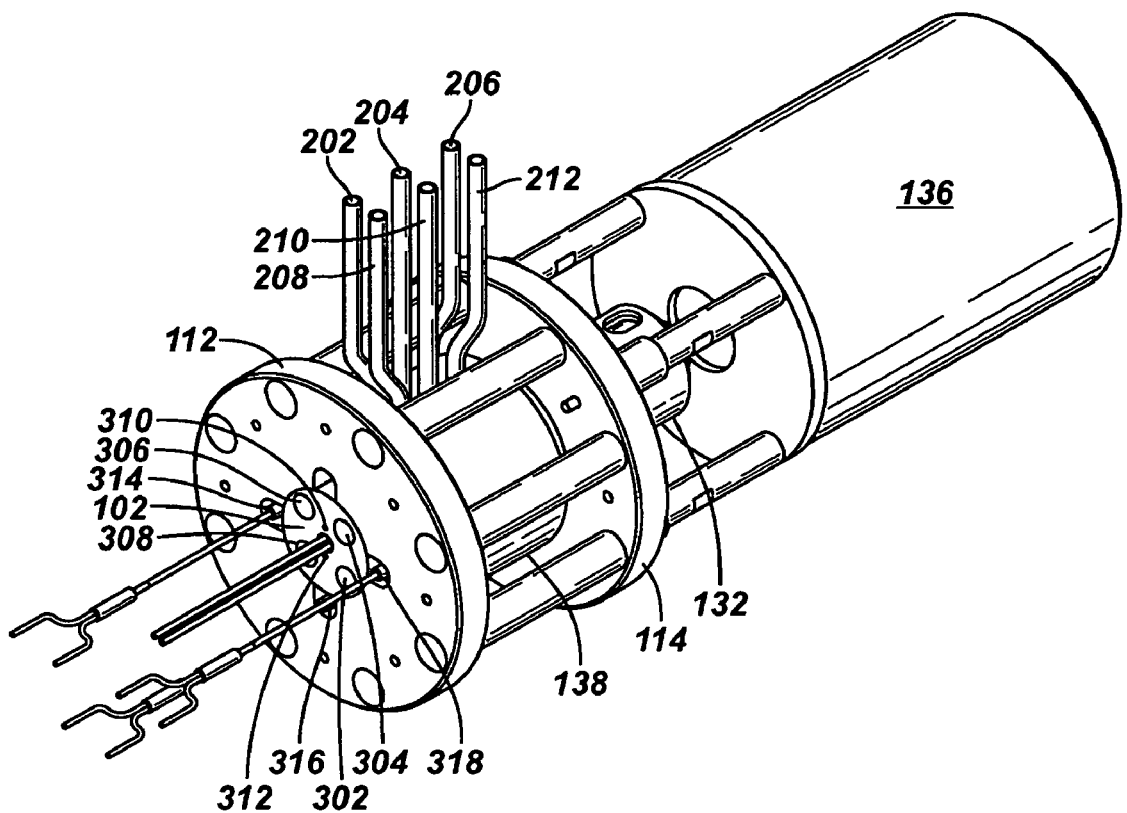
FIG. 2 is another view of a cylindrical Couette device according to an embodiment of the invention.
Figure 3:
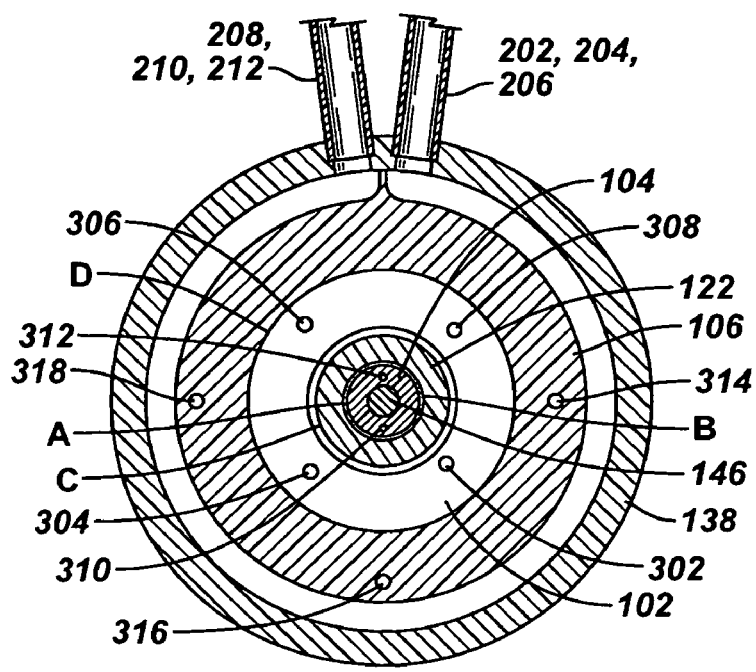
FIG. 3 is a top-down cross-sectional view of a cylindrical Couette device according to an embodiment of the invention.

One exemplary embodiment of a Couette device in accordance with some embodiments of the present invention is depicted in FIGS. 1–3. Generally, the device includes of a pressure-containing chamber within which an inner cylinder is affixed on bearings to the top and bottom walls of the cell. Rotation of the inner cylinder is driven through a magnetic coupling without the requirement for direct connection to a motor or other prime mover. This enables the cell to be operated at higher pressure than would be possible if a drive shaft were to penetrate the outer wall of the cell, in which case, a dynamic seal would be required.

Materials of construction were chosen based on operating parameters, pressure and temperature, as well as process fluid compatibility. Materials of construction and seals may be altered as necessary to meet changes in operating conditions.

Heat may be transferred to the cell through a heat cylinder wall. It may then be transferred through a small annulus to the rotating inner cylinder and subsequently to the sample fluid. The heat is then typically drawn from the cell through the outer wall into the fluid circulating through a jacket surrounding the outer cylinder. The jacket fluid may also transfer heat energy into the cell if its temperature is higher than the process fluid. There may also be further heat loss/gain, to a lesser extent, through the top and bottom walls of the cell. Also, additional heat may be generated through viscous heating caused by friction between the rotating inner cylinder and the process fluid. An insulating jacket may also be installed to minimize non-accounted heat loss (i.e., heat lost from the heat cylinder but not transferred to the circulated fluid).

The system may be instrumented as necessary to capture operating conditions and/or control the process. In this exemplary embodiment, there is provision for sensing: bulk jacket fluid inlet temperature; jacket fluid temperature for each of three chamber outlets; pressure differential between inlet and outlet of each of three jacket fluid chambers; static pressure of jacket fluid; outer wall temperature for nine locations (three radial locations, each with three axial locations within); bulk flow rate of jacket fluid; process fluid temperature at three radial locations; process fluid pressure; heater cylinder wall temperature at two radial locations; rotational speed of inner cylinder; and rotational speed of motor. The number of sensor locations is not crucial. Additional instrumentation may be added as desired. One such piece of additional instrumentation may be a torque sensor in the motor shaft, which may be used to resolve shear stress in the sample fluid at the inner cylinder wall.

Sample fluid is charged and evacuated through one or more of three ports arranged in suitable locations. Additional porting may be added, or existing porting removed, as desired.

Turning to the exemplary cylindrical Couette device of FIGS. 1–3, the boundary of the pressure containment zone is defined by the top wall 102, heater cylinder 104, outer cylinder 106, bottom wall 108, and magnetic drive cylinder 110.

The assembly is constrained by top 112 and bottom 114 retaining plates that are set apart by spacers 116 and secured by bolts 118 and nuts 120. The quantity of spacers may be altered as desired.

Seals between the following components contain the charged fluid: top wall 102 and outer cylinder 106; top wall 102 and heater cylinder 104; bottom wall 108 and outer cylinder 106; and bottom wall 108 and magnetic drive cylinder 110. The seal type and material are selected based on operating pressure, temperature and contained fluid.

Within the cell, the inner cylinder 122 is mounted on bearings 124, 126 and 128, coaxial to the outer cylinder 106, the heater cylinder 104, and the magnetic drive cylinder 110. The inner cylinder is able to rotate independently of both the outer cylinder 106 and the heater cylinder 104. A shaft is extended from the bottom of the inner cylinder to which an array of magnets 130 is secured. A similar magnet array 132 is attached, outside the pressure containment, to the shaft 134 of the motor 136.

The magnetic drive cylinder 110 is constructed of a non-magnetic alloy allowing unimpeded magnetic attraction between the outer magnet array 132 and inner magnet array 130. Through the magnet couple, a torque load may be applied to the inner cylinder 122, resulting in its rotation. The strength of the couple is a function of magnet material, number, size and arrangement.

A variable speed motor 136 is used to rotate the outer magnet array 132.

Surrounding the outer cylinder 106 is a multi-chamber (i.e., one or more chambers) circulation jacket 138 through which fluid is flowed. In one embodiment, there are three chambers; the quantity may be altered as desired. The fluid enters the jacket through inlets 202, 204, and 206, flows circumferentially around the cell through the chambers 140, 142, and 144 formed by the outer cylinder 106 and the jacket 138, and then exits the jacket through outlets 208, 210, and 212. The quantity of inlets and outlets may be altered as desired.

An internal heater 146 is confined in a cavity defined by the heater cylinder of the cell. The heater cylinder walls form a cavity, which is open to the top to allow the insertion of the heater core through the top wall 102, and to access wiring. The electric heater may be controlled using any number of temperature sensor locations as the control point. In one embodiment, a 300 W heater is used; however, this may be altered as desired. Also, in an alternative cylindrical Couette device, the heater may be directly incorporated into the inner cylinder and the heat cylinder 104 may be eliminated.

Fluid may be charged and evacuated to or from the cell through three ports 148, 150, and 302. Ports may be added or altered as desired.

Instrumentation in the device may be added or changed as necessary. In some embodiments of the invention, three thermocouple ports are as follows: 304, 306, and 308 in the top wall to allow for temperature measurement of the process fluid at three discrete radial distances; 310 and 312 in the heater cylinder wall to allow for temperature measurement within the wall at two discrete radial distances; 314, 316, and 318 in the outer wall to allow temperature measurement within the wall at three discrete radial distances; and further temperature sensors are mounted in the circulation fluid to measure both inlet and outlet temperatures. The quantity and location of sensors may be altered as desired. Also measured is the differential pressure between inlet and outlet of the circulation fluid chambers, as well as the cell pressure. In addition, the rotational speed of the inner cylinder is measured through the use of a proximity sensor 152. A torque sensor may be included, e.g., coupled to the motor shaft 134 to resolve the shear stress in the fluid at the inner cylinder wall.

A Couette device, according to some embodiments of the invention, is capable of operating at conditions comparable to field conditions, including pressures, temperatures, compositions (including, for example, sour fluids), surface materials and roughnesses, and shear (i.e., fully turbulent flow) comparable to field conditions. In some embodiments of the invention, the Couette device may operate at a pressure of at least about 15,000 psi and a temperature of at least about 200°C. In some embodiments of the invention, the Couette device may yield a Reynolds number for water of at least about 500,000.

Given such high maximum operating Reynolds numbers for water, it is possible for the sample fluid to be charged to the device while the device is generating turbulent flow, that is, flow without the presence of vortices in the annulus, and for such turbulent flow to be present throughout the run. As a result, the scale of the Couette device is not important, and a Couette device of essentially any size may be fabricated with the expectation that the results found for a particular sample under a particular set of conditions may be invariant across Couette devices of different size.

"Solids," as used herein, is meant one or more compounds dissolved or suspended in an industrial fluid. Solids may be organic (containing carbon) or inorganic (not containing carbon). In one embodiment, wherein the industrial fluid is crude oil, the solids may include one or more of asphaltenes, waxes, sulfur, or hydrates, as described above.

A fluid, as used herein, is any aqueous, organic or other liquid or gas carrying or potentially carrying materials in solution, suspension, emulsion, slurry, or other form. Any fluid used in industry may be studied according to the present method. For example, the fluid sample may be taken from a latex paint, an oil-based paint, a solvent, or other painting fluids; an aqueous or other fluid found in the food processing industry; a slurry of pulp found in the pulp and paper industry; suspensions found in the cosmetics industry; potable, semipotable, or non-potable water, either pre- or post-treatment; fluids used in cooling and processing in power generators, such as in nuclear reactors; process fluids used in, or fluid products of, the pharmaceutical industry; or crude oil or refined oil fractions from the petrochemical industry, among others. The foregoing list is not exhaustive.

In some embodiments of the invention, the fluid is a crude oil. Crude oil from many formations commonly contains solids, typically as one or more of waxes, asphaltenes, sulfur, minerals (e.g., scale), and hydrates. When crude oil is transported via pipe, such as from a formation to a wellhead via production tubing or from a wellhead or a storage vessel to a refinery via a pipeline, changes in the pressure, temperature, composition, or other parameters of the flowing crude oil may lead to deposition of solids. To clarify the terms "deposition" and "precipitation," the term deposition has often been used to describe the precipitation process. We do not use "deposition" in this way. While precipitation may be defined as the formation of a solid phase out of a liquid phase, deposition may be described as the formation and growth of a layer of the precipitated solid on a surface. Further, a necessary but not a sufficient condition for deposition is the precipitation of a solid phase from liquid solution. That is, although precipitation is a precursor to deposition, it does not necessarily ensure deposition. Moreover, whereas precipitation is mainly a function of thermodynamic variables such as composition, pressure and temperature, the deposition is also dependent on the flow hydrodynamics, heat and mass transfer, and solid-solid and surface-solid interactions.

"Precipitation," as used herein, refers to the agglomeration of solids while remaining suspended in the bulk fluid fraction. "Deposition," as used herein, refers to the falling out of suspension of the agglomerated solids and the resulting coating of the agglomerated materials on the interior wall of the pipe or tubing. As stated above, deposited solids may lead to reductions in the flow rate of the crude oil or other fluid in the pipe and require expensive and time-consuming cleaning of the pipe to restore the maximum flow rate of the crude oil or other fluid. Understanding at what pressures, temperatures, and other flow parameters precipitation or deposition are likely to occur in a sample of a particular crude oil or other fluid may allow a pipe operator or other user to maintain the crude oil or other fluid at flow parameters whereat precipitation or deposition are unlikely to occur, thus minimizing reductions in the flow rate of the crude oil or other fluid.

In the method, the fluid sample may be charged to a Couette device. In one embodiment, the Couette device is a cylindrical Couette device as described above.

In some embodiments of the invention, the charging step is performed isobarically, isothermally, or both.

In some embodiments of the invention, the Couette device is stored with water in its annulus, and charging involves displacing the water with the sample. Generally, all water or any other storage liquid may be fully removed from the Couette device prior to performing later steps of the method.

Once charged to the Couette device, the sample may be subjected to a pressure, a temperature, a surface type, a surface roughness, and a shear comparable to field conditions. The pressure may be reached by a sufficiently high rate or amount of sample charging. The shear may be reached by sufficiently rapid rotation of the inner cylinder, the outer cylinder, or both relative to each other.

Subjecting the sample to a pressure, a temperature, a surface type, a surface roughness, and a shear comparable to field conditions enables more realistic simulation of flow conditions in pipe and thus the method may provide results that more accurately reflect field conditions.

After the sample is undergoing turbulent flow, one or more of the pressure, temperature, composition, a surface type, a surface roughness, or shear of the sample may be changed. In one embodiment, the shear remains sufficiently high for the sample to remain under turbulence.

The pressure may be changed by changing the rate or amount of the sample charged to the Couette device; by changing the rate of amount of the sample drained from the Couette device; or by a combination thereof.

The temperature may be changed by changing the temperature of a heat exchange fluid; by internal heating of the contents of the Couette device; or by a combination thereof. Internal heating may be performed by use of a heating cartridge, by viscous heating, or both. The temperature may be changed to different extents at different portions of the Couette device, i.e., temperature gradients may be formed or maintained.

The composition may be changed by changing the proportions of two or more subsamples from which the sample is derived; by injecting an additional amount of the sample fluid; or by changing the phase.

The surface type and surface roughness may be "changed" by performing a experimental runs in each of a plurality of Couette devices, wherein the Couette devices differ in surface type, surface roughness, or both. A single Couette device which is modified between experimental runs provides a "plurality of Couette devices," as used herein.

The shear may be changed by changing the relative rotational speed of the inner cylinder to the outer cylinder.

The various techniques for changing the parameters described above are not to be considered an exhaustive list.

As a result of the change in one or more of pressure, temperature, composition, surface type, surface roughness, or shear, dissolved solids may precipitate or deposit on the interior walls of the Couette device. During or after the changing step, the type and amount of solids deposited on the interior walls of the Couette device may be quantified.

Quantification may be performed by any appropriate technique or apparatus, such as by sensing the type and amount of solids deposited on the interior walls or by removing solids from the interior walls and thereafter quantifying the type and amount. "Quantifying" is used herein to refer to both qualitative analysis, that is, whether particular solids, such as particular waxes, particular asphaltenes, or particular hydrates are present, and quantitative analysis, that is, what quantities of particular solids, such as particular waxes, particular asphaltenes, or particular hydrates are present. Techniques for quantification include, but are not limited to, gas chromatography, high performance liquid chromatography (HPLC), gel permeation chromatography, nuclear magnetic resonance (NMR), infrared spectroscopy, ultraviolet spectrophotometry, thin layer chromatography, and column chromatography, among others.

In some embodiments of the invention, the method further includes draining the sample from the Couette device. This may facilitate quantification by allowing deposited solids to be quantified in the device or by allowing deposited solids to be removed separately from the sample. The sample may be drained by gravity, by forced expulsion by application of a displacement fluid, such as helium, or other techniques.

In some embodiments of the invention, in which the method includes draining the sample, the quantifying step includes rinsing the interior walls with a solvent. The use of the solvent allows solids to be dissolved in the solvent. The resulting solution may then be extracted from the device and subjected to quantification, as described above.

The method may be performed, depending on the structure of the Couette device and the user's discretion, as a batch (or closed) process, a semibatch process, or a continuous (or open) process. A continuous process has the advantage of more closely simulating flow conditions in a pipe.

Emulsions, such as water-in-oil emulsions, may exist in fluid samples and may interfere with flow of the fluid in production tubing or pipeline or with fluid processing at a wellhead, a refinery, or a similar location, either as such or after undergoing a phase separation from other phases. Quantifying emulsions may be helpful in understanding the flow parameters of a fluid sample and improving handling of the fluid.

In some embodiments of the invention, the Couette device may be used to collect a solid deposit, and the techniques that are set forth below may be used to quantify and characterize this deposit. It is noted that the Couette device is one out of many possible mechanisms that may be used to collect the deposit and is used merely as an example herein for purposes of simplifying the following description.

Figure 4:
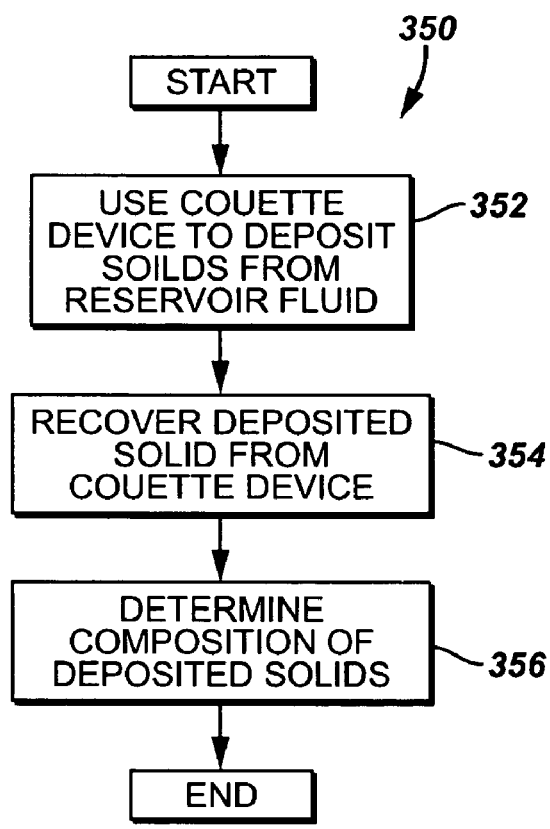
FIG. 4 is a flow diagram depicting a technique for deposition, recovery and characterization of chemical components of a solid deposition according to an embodiment of the invention.

The deposition on the interior surface of the Couette device may be rinsed for purposes of quantifying the chemical components that are present in the deposition. More specifically, referring to FIG. 4, in accordance with an embodiment of the invention, a technique 350 includes using (block 352) the Couette device to deposit solids from reservoir fluid. Thus, as described above, deposits from crude oils, condensate or bitumen are deposited in the Couette device under the simulated realistic production conditions of pressure, temperature, composition, surface type and roughness and shear regime. Next, in accordance with the technique 350, the deposited solid is recovered (block 354) from the Couette device. More specific details regarding the recovery of the deposited solid from the Couette device are described below. Subsequently, according to the technique 350, a detailed compositional characterization of the formed deposit is determined (block 356) using characterization data obtained from a combination of one or more techniques such as high resolution mass spectrometry, infrared, spectroscopic and nuclear magnetic resonance analyses.

The characterization data enables the identification, speciation and quantification of key chemical compounds that are responsible for deposition at the walls of production and transportation pipelines. Furthermore, the characterization data serves as key input to build robust compositional-based deposition models to predict and/or simulate the phase behavior of parent reservoir fluids and plan and/or optimize the corresponding production systems. Additionally, the characterization data enables the formation and/or synthesis of adequate solvents in chemicals to control and/or remediate the deposition of the solids. Lastly, the characterization data may also enable the development of suitable chemical sensors to continuously detect and monitor (in real time, for example) the deposition of the solids from reservoir fluids under typical production conditions in flow lines and surface facilities.

Figure 5:
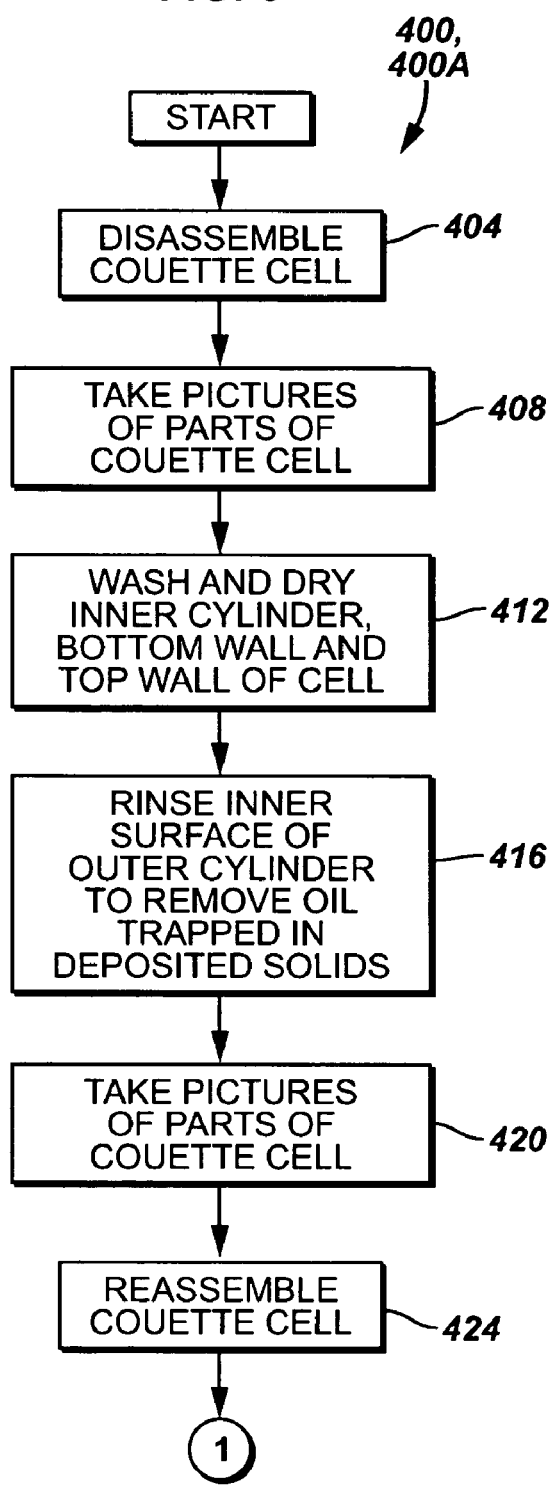
FIGS. 5 and 6 are flow diagrams depicting a technique to quantify chemical compounds present in a solid deposition according to an embodiment of the invention.

After the solid is deposited on the inner walls of the Couette device, extraction and recovery of the deposit may be performed in accordance with a technique 400 that is depicted in FIGS. 5 (flow chart 400a) and 6 (flow chart 400b).

Referring to FIG. 5, in accordance with the technique 400, after the deposition has been made on the interior walls of the Couette cell, the Couette cell is disassembled, as depicted in block 404. Next, in accordance with some embodiments of the invention, pictures may be taken (block 408) of the various disassembled parts (the inner cylinder, outer cylinder and top and bottom surfaces of the cell, for example) of the Couette cell.

The deposit is mainly observed on the interior wall of the outer cylinder of the cell. In some embodiments of the invention, the deposit on the interior wall of the outer cylinder is not rinsed with a solvent at this point. However, in accordance with some embodiments of the invention, the other components, such as the inner cylinder, the bottom wall and the top wall, are washed with a solvent, such as dichloromethane (for example), in accordance with block 412.

Although not rinsed with the solvent, the interior surface of the outer cylinder may be rinsed with a chemical to remove, or at least reduce, oil that is trapped in the deposited solid, as depicted in block 416. As a more specific example, in some embodiments of the invention, the interior wall of the outer cylinder may be rinsed with heptane. Additional pictures may be taken at this point, as depicted in block 420. Next, in accordance with the technique 400, components of the Couette cell are reassembled, as depicted in block 424. The Couette cell, in this assembled state may now be operated, as described below.

Figure 6:
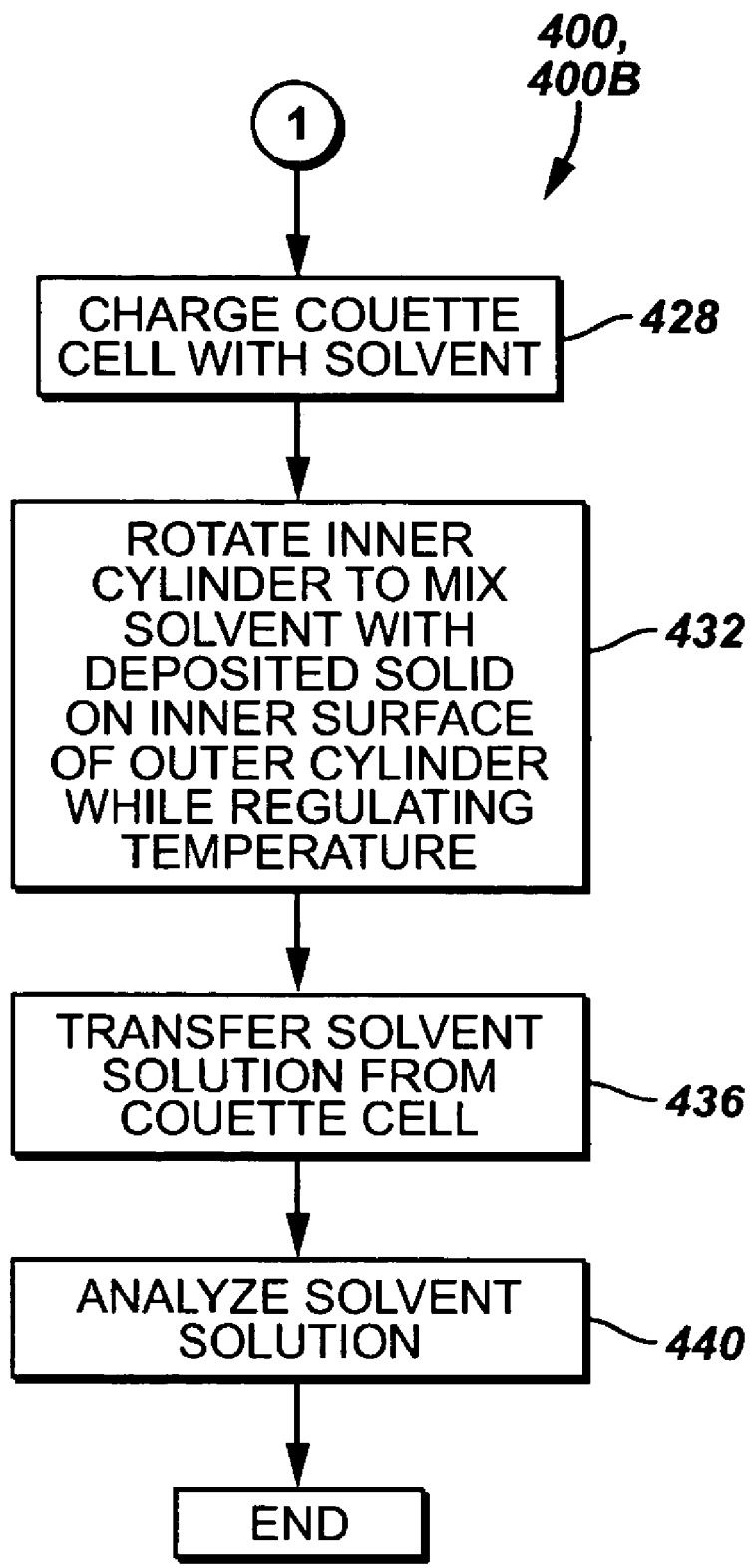

Referring to FIG. 6, continuing the technique 400, the Couette cell, now reassembled, is charged with a solvent, such as dichloromethane (as an example), as depicted in block 428. In other words, a particular pressure is applied to the solvent to force the solvent through the Couette cell into the chamber that is defined between the exterior wall of the inner cylinder and the interior wall (containing the deposit) of the outer cylinder.

In accordance with the technique 400, the inner cylinder is rotated (block 432) to mix the solvent with the deposited solid on the interior wall of the outer cylinder, as depicted in block 432. During this rotation, the temperature of the solvent is controlled, or regulated, and the rotation occurs during an interval of time, the duration of which depends on the nature of the deposit. In some embodiments of the invention, the inner cylinder is rotated at its maximum rotation to mix the solvent with the solid that is deposited on the interior wall of the outer cylinder.

The mixing of the solvent in the Couette cell produces a solvent solution that contains at least some of the dissolved deposit. This solution is transferred (block 436) from the Couette cell into a container, such as a glass bottle, for example. In accordance with the technique 400, the solvent solution is then analyzed (block 440) to quantify the chemical components that are present in the deposit.

Other steps may be used in other embodiments of the invention. For example, in some embodiments of the invention, a second rinse of the Couette cell may be performed to ensure that all deposit is recovered and the cell is indeed clean. Final pictures may then be taken of the clean parts of the Couette cell for a qualitative confirmation.

In some embodiments of the invention, the deposit contains asphaltenes that are subsequently analyzed using a combination of analytical techniques that include, for example, infrared spectroscopy, nuclear magnetic resonance imaging and Ultra-high resolution Fourier Transform Ion Cyclotron Resonance Mass Spectrometry (FT-ICR MS).

The results that are generated by the FT-ICR MS (for example) may then be compiled according to selective parameters. These parameters include functionality, the number of unsaturations and the carbon number.

A table 500 that is depicted in FIG. 7 illustrates a comparison of deposits to illustrate the effectiveness of the technique 400. Referring to FIG. 7, the table 500 includes a column 501 that lists various compound types in its rows. Thus, each entry in the column 501 identifies a particular compound, and the row has associated entries that reflect the percentages found of this particular compound. Column 504 of the table 500 depicts the percentages of the compounds (in column 501) found in the original "dead" oil (i.e., oil that has not been passed through the Couette cell). This data is presented for comparison with data 510 that was obtained in conjunction with the Couette cell.

The data 510 includes a column 520 that shows the percentages of the compounds (depicted in column 501) found in the production oil that was circulated through the Couette cell. Column 524 depicts the percentage compositions of the compounds (found in column 501) deposited on the spindle. Column 528 depicts the percentages of the chemical compounds (depicted in the column 501) that were deposited on the interior surface of the outer housing of the Couette cell. As may be seen, the deposition on the interior surface of the outer housing cylinder provides more information than the deposit on the spindle 524, for example.

While the present invention has been described with respect to a limited number of embodiments, those skilled in the art, having the benefit of this disclosure, may appreciate numerous modifications and variations therefrom. It is intended that the appended claims cover all such modifications and variations as fall within the true spirit and scope of this present invention.

What is claimed is:

1. A method comprising:
providing a deposition measuring device having a deposition from a fluid sample on an interior surface of the device;
charging the device with a solvent to produce a solvent solution containing the deposition;
using the solvent solution to quantify at least one chemical compound present in the deposition;
disassembling the deposition measuring device to separate the interior surface from other components of the deposition measuring device;
cleaning at least one component of the deposition measuring device other than the interior surface; and
reassembling the deposition measuring device,
wherein the charging is performed after the reassembly of the deposition measuring device.

2. The method of claim 1, wherein the fluid sample comprises a well reservoir fluid.

3. The method of claim 1, wherein the using comprises:
using at least one of mass spectrometry analysis, infrared spectroscopy analysis and nuclear magnetic resonance analysis.

4. The method of claim 1, wherein the deposition measuring device comprises an outer housing having the interior surface and an inner housing rotatably connected to the outer housing defining a space therebetween to receive the fluid sample when the deposition measuring device is assembled, and
the disassembling comprises at least disconnecting the outer housing from the inner housing so that the inner and outer housings are no longer rotatably connected.

5. The method of claim 1, wherein said at least one component comprises the outer housing.

6. The method of claim 4, wherein the outer housing comprises an upper interior wall surface and a lower interior wall surface further defining the space.

7. The method of claim 1, further comprising:
not cleaning the interior surface when the deposition measuring device is disassembled.

8. The method of claim 1, wherein the deposition measuring device comprises an outer housing having the interior surface and an inner housing rotatably connected to the outer housing defining a space therebetween to receive the solvent, the method further comprising:
rotating the inner housing with respect to the outer housing to produce the solvent solution.

9. The method of claim 8, wherein the space is adapted to receive the fluid sample to form the deposition.

10. The method of claim 8, wherein the deposition measuring device has a maximum speed at which the inner housing may rotate, and the rotating comprises rotating the inner housing at the maximum speed.

11. The method of claim 1, further comprising:
regulating a temperature of the solvent while producing the solvent solution.

12. The method of claim 1, further comprising:
before the charging, applying a fluid to the deposition to remove oil trapped in the deposition.

13. The method of claim 1, wherein the deposition comprises asphaltenes.

14. A method comprising:
providing a deposition measuring device having a deposition from a fluid sample on an interior surface of the device;
operating the device with a solvent to produce a solvent solution containing the deposition;
using the solvent solution to quantify at least one chemical compound present in the deposition;
disassembling the deposition measuring device to separate the interior surface from other components of the deposition measuring device:
cleaning at least one component of the deposition measuring device other than the interior surface; and
reassembling the deposition measuring device,
wherein the operating is performed after the reassembly of the deposition measuring device.

15. The method of claim 14, wherein the operating comprises:
operating at least one of a pressure regulator and a motor of the device.

16. The method of claim 14, wherein the fluid sample comprises a well reservoir fluid.

17. The method of claim 14, wherein the using comprises:
using at least one of mass spectrometry analysis, infrared spectroscopy analysis and nuclear magnetic resonance analysis.

18. The method of claim 14, wherein the deposition measuring device comprises an outer housing having the interior surface and an inner housing rotatably connected to the outer housing defining a space therebetween to receive the fluid sample when the deposition measuring device is assembled, and
the disassembling comprises at least disconnecting the outer housing from the inner housing so that the inner and outer housings are no longer rotatably connected.

19. The method of claim 14, wherein said at least one component comprises the outer housing.

20. The method of claim 18, wherein the outer housing comprises an upper interior wall surface and a lower interior wall surface further defining the space.

21. The method of claim 14, further comprising:
not cleaning the interior surface when the deposition measuring device is disassembled.

22. The method of claim 14, wherein the deposition measurement device comprises an outer housing having the interior surface and an inner housing rotatably connected to the outer housing defining a space therebetween to receive the solvent, and
the operating comprises rotating the inner housing with respect to the outer housing to produce the solvent solution.

23. The method of claim 22, wherein the space is adapted to receive the fluid sample to form the deposition.

24. The method of claim 22, wherein the deposition measuring device has a maximum speed at which the inner housing may rotate, and the rotating comprises rotating the inner housing at the maximum speed.

25. The method of claim 14, further comprising:
regulating a temperature of the solvent while producing the solvent solution.

26. The method of claim 14, further comprising:
before the operating, applying a fluid to the deposition to remove oil trapped in the deposition.

27. The method of claim 14, wherein the deposition comprises asphaltenes.

* * * * *